United States Patent [19]

Mueller et al.

[11] Patent Number: 5,086,778
[45] Date of Patent: Feb. 11, 1992

[54] METHOD AND SYSTEM FOR EVALUATING DATA PICKED-UP BY MEANS OF LONG TERM ECG DEVICES

[75] Inventors: Peter Mueller; Oscar Sebastiani, both of Munich, Fed. Rep. of Germany

[73] Assignee: Mueller & Sebastiani Elektronik GmbH, Munich, Fed. Rep. of Germany

[21] Appl. No.: 556,084

[22] Filed: Jul. 20, 1990

[30] Foreign Application Priority Data

Jul. 21, 1989 [DE] Fed. Rep. of Germany ....... 3924214

[51] Int. Cl.$^5$ ............................................. A61B 5/0402
[52] U.S. Cl. .................................... 128/696; 128/710; 364/413.06
[58] Field of Search ............................. 128/696, 710; 364/413.06

[56] References Cited

U.S. PATENT DOCUMENTS

| | | | |
|---|---|---|---|
| 4,535,783 | 8/1985 | Marangoni | 128/696 |
| 4,832,033 | 5/1989 | Maher et al. | 128/421 |
| 4,919,139 | 4/1990 | Brodard | 128/421 |

Primary Examiner—William E. Kamm
Assistant Examiner—Scott M. Getzow
Attorney, Agent, or Firm—Townsend and Townsend

[57] ABSTRACT

A method and a system of evaluating data picked-up by means of a long term ECG device and stored in a permanent memory, is characterized in that, in a first step, a transfer is effected of the data of the permanent memory onto a data carrier independent from the long term ECG device, with a brief evaluation of the data being simultaneously carried out; and in that, in a second step, the data transferred to the independent data carrier is subjected to detail evaluation at an evaluation center.

9 Claims, 1 Drawing Sheet

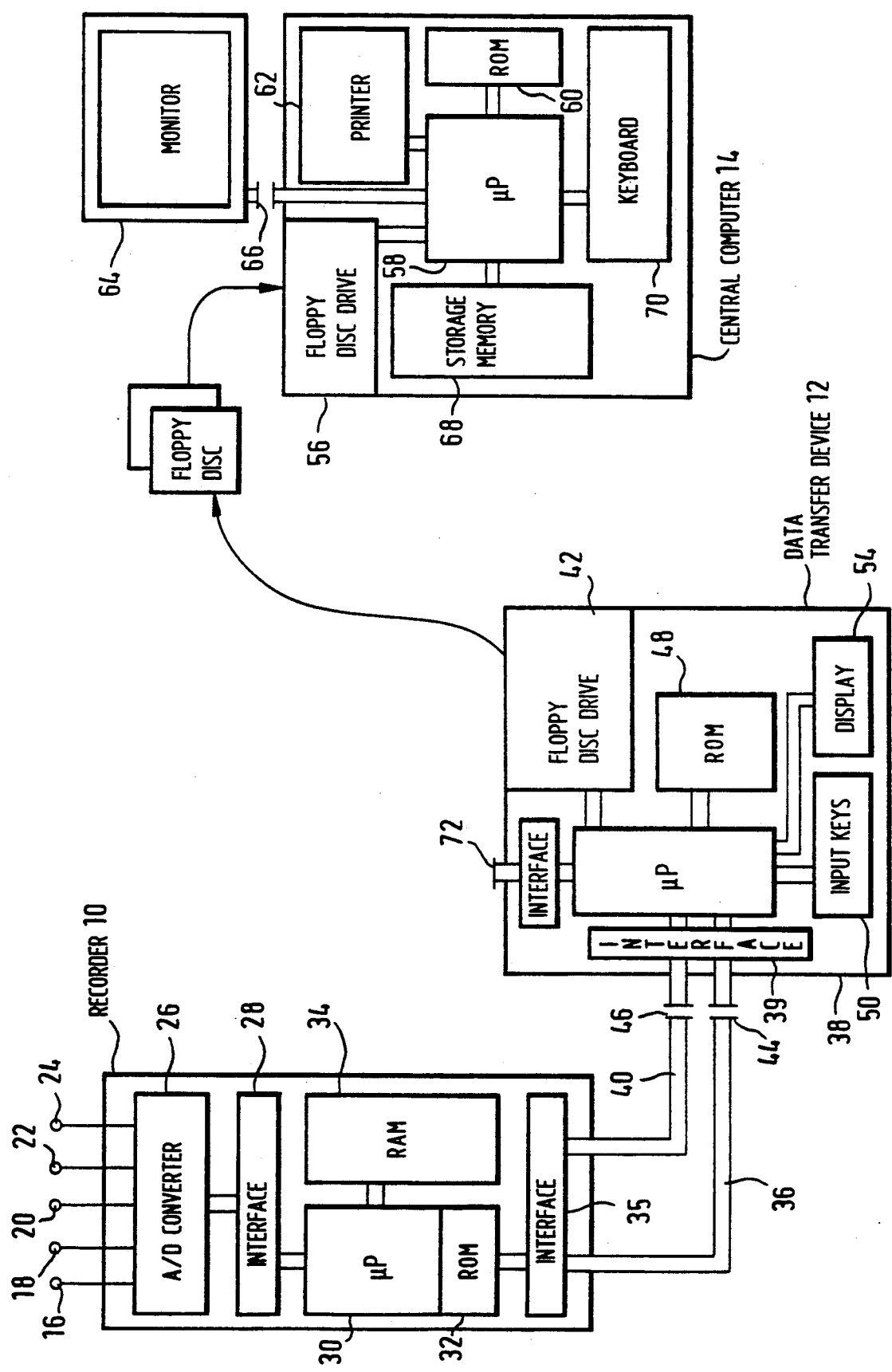

METHOD AND SYSTEM FOR EVALUATING DATA PICKED-UP BY MEANS OF LONG TERM ECG DEVICES

The invention relates to a method for evaluating data picked-up by means of a long term ECG device and stored in a permanent memory, and also to a system for the practical carrying out of this process.

Long term ECG devices ambulatory ECG devices which make it possible to monitor and record the heart activity of patients over longer periods of time, in particular over 24 hours, are in practical use in large numbers. The recording of the data takes place in permanent memories, in particular with devices of modern construction. As the evaluation devices required to evaluate the detected and stored data are relatively complex, and thus also costly, a central evaluation is, as a rule, effected for many such portable long term ECG devices. For this purpose it is necessary to take at least the fixed memory unit to the corresponding evaluation center, which, depending on the type of construction of the particular device, requires either the sending in of the whole piece of apparatus or the sending in of a removable memory unit.

In the former case the recording device is not available for a longer period of time, which is naturally undesirable and disadvantageous. The second case necessarily requires considerable technical complexity in the long term ECG device itself, since interchangeable memory units are relatively costly.

The object of the invention is thus to so design a method of the initially named kind that, on the one hand, ideal utilisation of the available long term ECG devices with permanent memories is possible and, on the other hand, that one can obtain a breakdown of at least the most important data of a recording procedure within the shortest possible time.

This object is satisfied in accordance with the invention essentially in that, in a first step, a transfer is effected of the data of the permanent memory onto a data carrier independent from the long term ECG device, with a brief evaluation of the data being simultaneously carried out; and in that, in a second step, the data transferred to the independent data carrier is subjected to detail evaluation at an evaluation center.

A substantial advantage of this method lies in the fact that the portable long term ECG device is immediately available again after the data transfer process, which takes only very little time, that a first diagnosis is possible after the brief evaluation and that the independent data carrier can be evaluated in detail at an evaluation center.

In the course of the brief evaluation a functional check of the total recording process is preferably carried out so that it is already clear at a very early time whether the total recording is in order, or whether the patient must at once be requested to carry the device for a further recording period. Thus time loss in reaching a diagnosis, which can under some circumstances be extremely negative, can be avoided.

The results of the brief evaluation are expediently made visible via an optical display. This can be realised without difficulties as a result of the restricted data output when compared with the total evaluation.

For the practical realisation of the method in accordance with the invention a system is provided in which a comparatively small, easy to handle intermediate device is provided which can be coupled with the portable long term ECG devices in order to ensure the play-over of the data recorded in the permanent memory of such devices onto a separate data carrier, which preferably comprises a floppy disk.

This intermediate device, which can be of priceworthy design, is preferably equipped with a brief evaluation unit which makes it possible, as a result of simple working processes, such as for example addition of events which are stored at certain storage locations, to obtain details which enable an initial diagnosis, with these details for example being made visible via an LCD display.

The existence of a single such intermediate device in the doctor's practice, or in a joint practice, group practice makes it possible to have a number of long term ECG devices almost continually in use and to simultaneously ensure that the final evaluation can be carried out rapidly and in uncomplicated manner, in addition to the extremely advantageous initial evaluation. This is possible because it is particularly simple and comfortable to transmit floppy disks, onto which the corresponding data has been transferred in the form of an identical copy, to an evaluation center. The despatch of such floppy disks can take place in the manner of a letter by the normal postal route.

A further advantage of the use of correspondingly formatted floppy disks for the detailed evaluation lies in the fact that the documentation of all the evaluations carried out in the evaluation center can also be centrally effected, so that it is sufficient to send the relevant doctor the actual diagnosis.

BRIEF DESCRIPTION OF THE DRAWING

The drawing is a diagram which schematically illustrates the present invention.

DESCRIPTION OF THE PREFERRED EMBODIMENTS

As shown in the drawing the system of the invention comprises three basic pieces of equipment, namely a recorder 10, a data transfer device 12 and a central computer 14. In practical use the central computer 14 would be owned and maintained by, for example, a hospital or a number of collaborating doctors, and each doctor would have one data transfer device 12 and several recorders 10. Each patient being investigated is given a recorder 10 by the doctor and this recorder enables an electrocardiogram to be recorded from the patient over a period of 24 hours.

In recent years long term ECG monitoring (Holter monitoring) has become increasingly important. It is often the only non-invasive possibility for obtaining important information on the cardial state of the patient. In this respect it is very important that both waking and also rest phases of the patient are detected. The patient should be in his customary environment and should also pursue his normal daily routine. Thus the ECG recorder accompanies the patient over the envisaged time interval, typically 24 hours. The patient is connected to the recorder via five electrodes 16, 18, 20, 22 and 24, the signals of which are passed via an analog digital converter 26 and a suitable interface, for example a parallel or serial interface 28 to a microprocessor 30 which includes ROM storage elements typically EPROMs containing the programs necessary for the operation of the microprocessor. The ECG derivation takes place via the five electrodes with three channels and the system, that is to say, the microprocessor under control of the ROM elements 32, automatically selects the two most favourable derivations with the best input signal for analysis. The device thus measures the signals on two independent derivations and records these continuously in the RAM permanent memory element 35 which is connected to the microprocessor by a suitable bus. In the present application all busses are shown as dual lines. In addition the CM 5 derivation is measured for ST measurement. During the monitoring period each QRS complex is analysed in real time and classified. The ECG is also checked for ST path changes. Often these do not occur even under load (exercise cardiogram) so that the doctor must frequently turn to the long term ECG as a reliable diagnostic tool.

For the diagnosis of silent ischaemia the ST analysis is becoming increasing important. Since no standard derivations are used for long term ECG, and as artefacts are often superimposed on the signals, the following requirements must be satisfied for a reliable ST analysis:
high sampling rate (2 milliseconds)
three channel analysis
unfiltered ECG
reliable I- and J-point detection.

If an unfiltered ECG is available then a reliable recognition of the I- and J-point is only possible using the averaging process. In this 16 QRS complexes are averaged out (not filtered). As the disturbances are random and do not occur periodically they are eliminated with this process. This analysis is all carried out by the microprocessor 30 under control of the ROM 32 and is stored in the RAM 34.

When the recording is complete the patient returns to the doctor (or the doctor visits the patient) and the recorder 10 is plugged into the data transfer device 12. There are two basic connections here, first of all control lines 36 which extend between the interface 50 and the interface 39 to the microprocessor 38 for the transfer of signals from and to the microprocessor 30 and also data lines 40. The data lines 40 likewise extend between the interface 35 and the microprocessor 38 for the transfer of data from the RAM 34 into the microprocessor which subsequently serves to record the data in the appropriate format on two floppy disks placed one after the other in the floppy disk drive 42 embodied in the data transfer device 12. The floppy disk drive could be a twin disc drive but is preferably a less expensive single disk drive. This means the operator has to change the floppy disk during the transfer process for which he receives a cue from the data transfer device. Two floppy disks are required in order to store the data picked up by the recorder 10 in a 24 hour recording period. A suitable interface is present between the microprocessor and the floppy disk drive(s) but is not shown in the drawing.

The double lines 44 and 46 in the control lines 36 and the data lines 40 represent a plug and socket connector.

The data transfer device 12 includes, in addition to the microprocessor 38 and the floppy disk drive 42, the usual ROM 48 typically in the form of EPROMs which is associated with the microprocessor and contains a suit of program for its operation, and also input keys 50. The input keys make it possible for the doctor to start and stop the data transfer device and also make it possible for him to feed in patient-related data (name, address, age, etc.) and to initiate the brief evaluation. Furthermore, prior to handling the recorder 10 to the patient it is plugged into the data transfer device 12 and the doctor can start the recorder, i.e. start the next reading on the next particular patient. At this stage the doctor can, if desired, already input the patient specific data, including the limits of tachydardias, barchydardias, etc. so that this data is stored in the RAM and is then subsequently transferred direct to the floppy disks when transferring the data from the RAM 34 onto the floppy disks. The programs for the operation of the recorder 10 are stored therein in ROM 32.

The data transfer device 12 has a built-in display 54 (for example an LED display) which enables the doctor to verify the information he has keyed in and also enables him to view the results of a brief analysis of the data recorded by the recorder 10.

The data contained in the RAM 34 is namely investigated in the data transfer device 12, by the microprocessor 38 under the control of the programs in the ROM 48, to produce information concerning pathological events during the ECG recording. This is a numerical evaluation which is known per se for the evaluation of ECG data. In particular the brief evaluation involves the numerical evaluation of the following parameters: Tachycardia, bradycardia, couplets, nerve pulses (volleys), asystolia, markings.

The results of this analysis, which is shown on the display 54 (and if desired also printed out on an optical printer (not shown)), can be viewed by the doctor so that he can make an initial diagnosis and, if necessary, instigate the relevant treatment.

After the two floppy disks have been prepared, an exercise which takes just a couple of minutes, they are sent, for example by post, to the evaluation center where the central computer 14 is located. Here the floppy disks are placed in the floppy disk drive 56 which is controlled by a microprocessor 58 having its own suite of programs which are held in read only memory 60 typically in the form of EPROMs. This suite of programs enables a full evaluation of the data relating to the electrocardiogram to be effected and the results are printed out on the printer 62 and can optionally also be displayed on the monitor 64 which is connected (if provided) to the computer 14 via the plug and socket connector 66.

During evaluation the data is stored in a storage memory 68 of the central computer. The central computer 14 also has its own keyboard 70 which enables the medical staff to call up the information which they wish to examine on the monitor and also permits them to make comparisons between new and old records from the same patient. Of course the keyboard also serves for all other functions of the central computer by the operator.

If the patient related data is stored on the floppy disks, which is the preferred arrangement, then this data is read in automatically read in via the floppy disk drive. If, on the other hand, the patient related data is simply written by hand on a lable on the floppy disk then it must first be keyed in to the central computer 14 at the keyboard 70 by the operator.

After evaluation by the central computer the disks are stored (archived) as a permanent record. They form a low cost storage medium which takes up little space so that they can be retained for long term investigations and inserted into the floppy disk drive 56 of the central computer 14 for carrying out comparisons or for looking again at special or reviewing events which can be specifically called up as desired, e.g. using the keyboard 70. The results of the detailed evaluation can be written onto the floppy disk by the central computer 14, so that it is immediately available again for comparison purposes (since it is stored on the floppy disk).

The recording device in accordance with the present invention has typical dimensions of 4 cm high, by 8 cm wide, by 15 cm deep and a weight of 0.300 kg.

A simple baby cell of 1.5 V provides a sufficient power supply. In addition a back-up nickel cadium accumulator is built-in to the recorder for data security. This means that the recorder can hold the data from one patient for up to three weeks. As previously mentioned the recorder has three ECG amplifier channels and the analysis takes place on three channels simultaneously. The sampling rate of frequency is 500 Hz, or 2 ms per channel. The frequency range is 0.02 to 100 Hz and a marking key is present. The interfaces comprise two 14 pole sockets for data and control signals. Validation can be carried out with MIT/AHA reference bands, e.g. at the University clinic in Cologne or the Alba Albert Ludwid University in Freibourg. Various options that are available comprise apnoea measurement and O$_2$ saturation measurement.

The data transfer device has a height of 10 cm, a width of 23.5 cm and a depth of 23.5 cm, it weighs 2.9 kg and has a standard 220 V supply with a maximum current requirement of 70 mA. There is a battery buffered (Ni-Cd) real time clock. The floppy disks used are 3.5 inch size with a capacity of 1.44 megabyte. The inbuilt display will typically be an LCD display and the interfaces for the ECG output are an analog 2-channel (1 mV/1 V) RS232C 24 pol.

To summarise, the operation of the device is as follows:

The recorder is first started and programmed to carry out sepcial functions using the data transfer device 12. The application of the electrodes to the patient can be monitored via an analog output e.g. by an ECG pen recorder which is attached to the data transfer device 12 (at the analog output 72 (the pen recorder is not shown). The recorder then carries out a 24 hour electrocardiograph with real time analysis and ST measurement. The results being stored in the RAM 34 of the recorder 10.

At the end of the recording time the recorder 10 is connected to the disk transfer device 12 and the data is played over from the RAM 34 of the recorder 10 onto two floppy disks placed in sequence in the floppy disk drive 42 of the data transfer device 12. At the same time a brief evaluation of the ECG data is carried out and the results of this investigation are shown on the display 54 built into the data transfer device 12. After the data has been recorded on the two 3.5 inch floppy disks, these are sent to the central evaluation computer 14 for full evaluation and storage.

We claim:

1. A method of evaluating data picked-up by means of a long term ECG device and stored in a permanent memory, characterised in that, in a first step, a transfer is effected of the data of the permanent memory onto a data carrier independent from the long term ECG device, with a brief evaluation of the data being simultaneously carried out; and in that, in a second step, the data transferred to the independent data carrier is subjected to detailed evaluation at an evaluation center.

2. Method in accordance with claim 1, characterised in that during the brief evaluation a functional check is carried out of the total recording process.

3. Method in accordance with claim 1, characterised in that the results of the brief evaluation are made visible via an optical display.

4. Method in accordance with claim 1 characterised in that during the brief evaluation at least the number of the pathological and serious events for the judgement of the ECG are detected.

5. Method in accordance with claim 1 characterised in that the transfer of the data from the permanent memory to the independent data carrier takes place in the form of an identical copy.

6. System including a portable long term ECG devices with an inbuilt permanent memory, characterised by a central evaluation unit and a plurality of intermediate device means for transferring the data of the long term ECG devices onto an independent data carrier and also for carryng out a brief evaluation of the data.

7. System in accordance with claim 6, characterised in that the intermediate device is connectable with long a term ECG device via a plug coupling.

8. System in accordance with claim 6, characterised in that the independent data carrier comprises a floppy disk.

9. System in accordance with claim 6 characterised in that the intermediate device has an LCD display for the result of the brief evaluation.

* * * * *